| United States Patent [19] | [11] Patent Number: 4,783,142 |
|---|---|
| Mutzhas | [45] Date of Patent: Nov. 8, 1988 |

[54] RADIATION PROTECTION FILTER

[76] Inventor: Maximilian F. Mutzhas, Sonnenstr. 17/Eing. Joseph-Spital-Str. 14, D-8000 München, Fed. Rep. of Germany

[21] Appl. No.: 51,746

[22] PCT Filed: Sep. 12, 1986

[86] PCT No.: PCT/EP86/00525

§ 371 Date: Apr. 23, 1987

§ 102(e) Date: Apr. 23, 1987

[87] PCT Pub. No.: WO87/01817

PCT Pub. Date: Mar. 26, 1987

[51] Int. Cl.$^4$ ............................ G02B 5/20; G02C 7/10
[52] U.S. Cl. ..................................... 350/311; 350/438; 351/163; 252/582; 252/589
[58] Field of Search ................ 350/311, 314, 1.7, 438; 351/163; 252/582, 588, 589

[56] References Cited

U.S. PATENT DOCUMENTS

| 3,887,485 | 6/1975 | Neuroth | 350/311 |
|---|---|---|---|
| 3,909,441 | 9/1975 | Ohyama et al. | 252/589 |
| 4,200,360 | 4/1980 | Mutzhas | 252/589 |
| 4,238,351 | 12/1980 | Alfes et al. | 252/589 |
| 4,643,537 | 2/1987 | Vance | 350/438 |
| 4,674,823 | 6/1987 | Epstein | 350/1.7 |

FOREIGN PATENT DOCUMENTS

| 1954802 | 3/1971 | Fed. Rep. of Germany . |
|---|---|---|
| 2276601 | 1/1976 | France . |
| 2343267 | 9/1977 | France . |

Primary Examiner—John K. Corbin
Assistant Examiner—Loha Ben
Attorney, Agent, or Firm—Learman & McCulloch

[57] ABSTRACT

The invention relates to a radiation protection filter for skin pigmentation during solar irradiation. The light transmittance of the radiation protection filter in the wavelength range between 380 and 780 nm is such that, when the radiation protection filter is used, the amount of radiation that penetrates the eye lens in the 340 to 400 nm range is, at the very most, that amount which would penetrate the eye lens when the radiation protection filter is not used. Radiation-caused eye damage is thus prevented.

7 Claims, No Drawings

RADIATION PROTECTION FILTER

The invention relates to a radiation protection filter for skin pigmentation during solar irradiation.

For medical reasons, it is necessary to occasionally expose the skin of the human body to natural solar irradiation. The pigmentation resulting from the effect of certain spectral ranges not only provides an attractively tanned appearance corresponding to today's cosmetic fashion trends, but also shields unprotected skin from hazardous solar radiation. The pigmentary infiltration of the skin thus, to a large degree, protects against erythema-effecting radiation with a wavelength of less than 320 nm.

In order to achieve skin tanning in the fastest, most agreeable and physiologically safe manner during solar irradiation or irradiation with artificial radiation sources, the applicant has already developed a radiation protection filter made of a plastic with an incorporated radiation-absorbing material (DE-OS No. 26 09 194). This radiation-absorbing material blocks any physiologically harmful radiation with a wavelength shorter than 320 nm, filters out radiation over 450 nm as much as possible, and provides the highest possible transmittance in the intermediate range.

Now, it is a known fact that, apart from acute inflammations after lengthy exposure, radiation with a wavelength shorter than 340 nm can also lead to irreversible dimness (cataracts) in the lens of the human eye. Recent studies have shown that radiation in the 340 to 400 nm range can also cause such eye damage. On the other hand, radiation in the 340 to 440 nm range can be used to achieve skin tanning with healthy persons without the risk of sunburn, skin cancer or premature skin ageing.

The object of the invention is thus to design a radiation protection filter for skin pigmentation during solar irradiation in such fashion that radiation-caused eye damage is avoided. Inasmuch as the radiation protection filter is used in the form of tanning eyeglasses, it is to be designed in such fashion that, on the one hand, the skin area covered by the glasses around the eyes will be sufficiently tanned, whereas, on the other hand, radiation-caused eye damage is prevented.

The object of the invention can be achieved by maintaining the following relationship between the radiation wavelength and the mean transmittance of the filter:

| Wavelengths (nm) | Transmittance |
| --- | --- |
| 300–340 | 0.1 maximum, more preferably 0.01, and most preferably 0.001 |
| 340–400 | 0.35–0.55 |
| 340–440 | 0.45–0.7 |

In addition, the objective of the invention can best be met in respect of radiation in the wavelength range between 380 and 780 nm if the protection filter's light transmittance is such that, when the filter is used, the amount of radiation in the range between 340–400 nm that penetrates the eye lens does not exceed that amount of radiation in the 340–400 nm range which penetrates the eye lens when the filter is not used.

The inventive doctrine is based on the considerations described in the following. With regard to the symbols used therein, reference is made to the list of symbols at the end of the description.

The radiation penetrating the lens of the human eye is determined by the irradiance in the pupillary plane and by the pupillary surface area (i.e. the size of the pupil in the iris). The pupillary surface area, in turn, is regulated in the case of healthy persons of medium age by the illumination $E_{vis}$ in the pupillary plane. Since it is very difficult to measure the irradiance or illumination in the pupillary plane directly, the corresponding tangential values for the front side of the eye (cornea irradiance or cornea illumination) normal to the line of vision are used for calculation.

The invention proceeds from the assumption that the risk of lens damage (cataracts) from solar irradiation of the unprotected eye in the 340 to 400 nm range is tolerable for a healthy person. Proceeding from this assumption, the invention provides that, in the case of protected eyes (i.e. when the radiation protection filter is used), this radiation (in the 340 to 400 nm range) cannot enter the eye lens in excess of the amount entering the lens of an unprotected eye. On the other hand, the invention enables the maximum possible amount of skin-tanning-effective radiation in the range between 340 and 440 nm to reach the skin area covered by the radiation protection filter.

The basis requirement for the invention is thus:

$$\phi_{31} \leq \phi_{30} \tag{1}$$

Since the radiant flux is equivalent to the product of the irradiance and the pupillary surface area, the following equations can be set up:

$$\phi_{30} = E_{30} \cdot F_o \tag{2}$$

$$\phi_{31} = E_{31} \cdot F_1 \tag{3}$$

$$E_{p,30} = E_{30} \cdot f_3 \tag{4}$$

$$E_{p,31} = E_{31} \cdot f_3 \tag{5}$$

The following interrelationship exists between the irradiance $E_{31}$ for eyes protected with the radiation protection filter (in the 340 to 400 nm wavelength range), the irradiance $E_{30}$ for unprotected eyes and the mean transmittance $\tau_3$ (for the 340 to 400 nm wavelength range):

$$E_{31} = E_{30} \cdot \tau_3 \tag{6}$$

The following results from (1)–(6):

$$F_1 \leq \frac{F_o}{\tau_3} \tag{7}$$

The light transmittance $\tau_{vis}$ can generally be determined from the following correlation:

$$\tau_{vis} = \frac{\int_{380}^{780} E(\lambda) \cdot v(\lambda) \cdot \tau(\lambda) \cdot d\lambda}{\int_{380}^{780} E(\lambda) \cdot v(\lambda) \cdot d\lambda} \tag{8}$$

The following interrelationship exists between the cornea illumination $E_{vis,1}$ for eyes protected with the radiation protection filter, cornea illumination $E_{vis,o}$ for unprotected eyes and the light transmittance $\tau_{vis}$:

$$E_{vis,1} = E_{vis,o}\tau_{vis} \qquad (9)$$

In addition to this, the pupillary surface area F has the following interrelationship with cornea illumination $E_{vis}$:

$$F = 0.0984 \cdot \ln^2 E_{vis} - 2.8798 \cdot \ln E_{vis} + 21.0625 \qquad (10)$$

If equations (7), (8), (9) and (10) are evaluated for various values of $\tau_3$ and $E_{vis}$, an interrelationship between $\tau_{vis}$ and $\tau_3$ is arrived at which can be approximated with the following equation:

$$\tau_{vis} \geq \tau_3^2 - \frac{(1-\tau_3)^2}{10} \qquad (11)$$

Thus, if one provides that the light transmittance $\tau_{vis}$ has a minimum value determined by $\tau_3$, then it is ensured that the maximum amount of radiation in the 340 to 400 nm range entering the eye lens when the radiation protection filter is used is that amount which enters the lens when the radiation protection filter is not used.

The mean transmittance $\tau_1$, $\tau_2$, $\tau_3$, $\tau_4$ and the light transmittance $\tau_{vis}$ are affected through the inclusion of organic, UV-absorbing substances and organic soluble coloring materials or pigments or anorganic pigments in the plastic material of the radiation protection filter.

The following are particularly suitable as UV-absorbing substances: benzophenones, benzotriazoles, salicylic-, cinnamic- and oxalic-acid compounds and compound resulting from these substances by means of modification.

Proceeding from the internal transmittance $\tau_i(\lambda)$, which is linked to the correction factor $R_F$ and the transmittance $\tau(\lambda)$ by the equation $$\tau_i(\lambda) = \frac{\tau(\lambda)}{R_F} \qquad (12)$$

one can, by applying Lambert's law, $$\tau_{i,2}(\lambda)^{k1} = \tau_{i,1}(\lambda)^{k2} \qquad (13)$$

calculate the desired spectral transmittance curve for the radiaton protective filter through alteration of the additive concentration of UV absorbers and coloring materials. The values of $\tau_1$, $\tau_2$, $\tau_3$, $\tau_4$ and of $\tau_{vis}$ can be determined from this.

The invention is described in more detail below using several examples.

The underlying assumption here is that the cornea illumination does not exceed the value $E_{vis,o} = 50,000$ lx under normal solar irradiation conditions; this value is selected for the following examples.

EXAMPLE 1

The objective is for a pair of violet-colored sunglasses to have the following transmittance values:

$\tau_2 \leq 0.02 \quad \tau_{vis} \leq 0.35$ $\tau_3 = 0.45$ $\tau_4 = 0.55$

The intended impact strength is $\geq 30$ kJ·m$^{-2}$.

With $E_{vis,o} = 50,000$ lx, the pupillary surface area $F_o$ of the unprotected eye can be determined by mean of equation (10) as being 1.42 mm$^2$. The maximum admissible pupillary surface area $F_1$ for the unprotected eye thus results from equation (7) as being 3.15 mm$^2$.

By inserting the value of $\tau_3$ in equation (11), one obtains $\tau_{vis} \geq 0.172$.

It then follows from equation (9) that $E_{vis,1} = 8600$ lx.

If this value is inserted in equation (10), the result is that $F_1 = 3.05$ mm$^2$.

This pupillary surface area is thus smaller than the maximum admissible pupillary surface area of 3.15 mm$^2$.

In order to achieve the required impact strength, 1.5 mm thick polycarbonate (PC) is selected as the base material of the radiation protection filter.

The requirements with regard to the transmittance values can be fulfilled if the following materials are used: UV absorber 103 (Matzhas Produktions-Gmbh, Munich), as the sharp-cut absorber, and coloring material 205 (Mutzhas Produktions-GmbH, Munich).

The directed spectral transmittance of the following materials in the 25 to 780 nm range is then determined:

Polycarbonate without UV absorbers and coloring materials,

Polycarbonate with UV absorber 103, and

Polycarbonate wiith coloring material 205.

By applying the previously mentioned Lambert's law (equation 13), the spectral transmittance curve desired for the sunglasses can be calculated through alteration of the UV absorber and coloring material concentrations. The values of $\tau_1$, $\tau_2$, $\tau_3$, $\tau_4$ and of $\tau_{vis}$ result from this.

The resultant formula for the injection mold granules used for manufacturing the sunglasses is as follows:

97.5% polycarbonate granules 2.2% UV absorber 103

0.3% coloring material 205.

The violet-colored sunglasses have a $\tau_{vis} = 0.31$ (which is substantially more than the minimum value 0.172) if $\tau_3 = 0.45$ and $\tau_4 = 0.55$. Consequently, $\phi_1:\phi_o = 0.77$.

Under these conditions, only 77% of the radiation between 340 and 400 nm—compared with unprotected eyes—enters the eye lens when the sunglasses are used.

EXAMPLE 2

The objective is blue-colored sunglasses with the following values:

$\tau_2 \leq 0.001 \quad \tau_{vis} \leq 0.03$ $\tau_3 \geq 0.4$ $\tau_4 \geq 0.5$ Impact strength $> 12$ kJ·m$^{-2}$.

If impact-resistant, 2.5 mm thick polymethyl methacrylate (PMMA with butyl acrylate) is used as the material, the following formula results when the method described in Example 1 is used:

98.5% polymethyl methacrylate granules, impact-resistant, 1.4% UV absorber 105 (Mutzhas Produktion-GmbH), 0.1% coloring material 214 (Mutzhas Produktions-GmbH).

The transmittance values are as follows:

$\tau_2 \leq 0.001$ $\tau_3 = 0.41$ $\tau_4 = 0.53$ $\tau_{vis} = 0.26$ $\phi_1:\phi_o = 0.75$

EXAMPLE 3

The objective is grey-colored sunglasses with the following data:

$\tau_2 \leq 0.01$   $\tau_{vis} \leq 0.4$ $\tau_3 \geq 0.35$ $\tau_4 \geq 0.45$ Impact strength $>60$ kJ m$^{-2}$.

If impact-resistant, 2.0 mm thick cellulose propionate is used as the material, then application of the method described in Example 1 results in the following formula:
98% cellulose propionate granules, impact-resistant
1.8% UV absorber 106 (Mutzhas Produktions-GmbH)
0.2% coloring material 249 (Mutzhas Produktions-GmbH).

The resultant sunglass specifications are as follows:

$\tau_2 \leq 0.001$ $\tau_3 = 0.36$ $\tau_4 = 0.46$ $\tau_{vis} = 0.35$ $\phi_1:\phi_2 = 0.59$

EXAMPLE 4

The objective is to manufacture red-violet colored filter plates to cover sun terraces (domelights, windows, water and land vehicle glasswork, etc.) with an impact strength of $\geq 40$ kJ m$^{-2}$ and the following transmittance values:

$\tau_2 \leq 0.01$ $\tau_3 \geq 0.45$ $\tau_4 \geq 0.55$ $\tau_{vis} \leq 0.25$

If impact-resistant 4 mm thick acrylonitrile methyl methacrylate (AMMA) is used as the material, the resultant formula is as follows:
99% acrylonitrile methyl methacrylate
0.8% UV absorber 102 (Mutzhas Produktions-GmbH)
0.2% coloring material 204 (Mutzhas Produktions-GmbH)

The following data are achieved with this:

$\tau_2 \leq 0.001$ $\tau_3 = 0.46$ $\tau_4 = 0.56$ $\tau_{vis} = 0.20$ $\phi_1:\phi_o = 0.93$

EXAMPLE 5

The objective is a filter film to cover shades (awnings, tents, etc.) that has the following transmittance values:

$\tau_2 \leq 0.001$ $\tau_3 \geq 0.3$ $\tau_4 \geq 0.4$ $\tau_{vis} < 0.15$

The film is to be violet-colored and flexible.

If 0.3 mm-thick soft PVC film is used, the resultant formula using the above-mentioned calculation mode is as follows:
95% soft PVC
4.5% UV absorber 101 (Mutzhas Produktions-GmbH)
0.5% coloring material 206 (Mutzhas Produktions-GmbH).

The film specifications are then as follows:

$\tau_2 \leq 0.001$ $\tau_3 = 0.36$ $\tau_4 = 0.48$ $\tau_{vis} = 0.1$ $\phi_1:\phi_o = 0.93$

EXAMPLE 6

The objective is to coat glass or plastic with a violet-colored filter varnish that possesses the following properties for sunglasses, vehicle sunroofs, flexible shades, etc.:

$\tau_2 \leq 0.01$ $\tau_3 \geq 0.35$ $\tau_4 \geq 0.45$ $\tau_{vis} \leq 0.20$

If acryllic varnish is used, the resultant formula for a dry layer thickness of 0.01 mm is as follows:
91% acrylllic varnish (50% non-volatile matter)
8% UV absorber 104 (Mutzhas Produktions-GmbH)
1% coloring material 207 (Mutzhas Produktions-GmbH).

The resultant specifications are as follows:

$\tau_2 \leq 0.001$ $\tau_3 = 0.40$ $\tau_4 = 0.53$ $\tau_{vis} = 0.15$ $\phi:\phi_o = 0.90$ Two aspects should be mentioned in conclusion:

The scope of validity of equation (8) extends from 0.005 1× (equivalent to an apparent pupil width, i.e. an externally visible pupil diameter, of 8 mm and to a size of pupil in the iris of 7.14 mm) to 50,000 1× (equivalent to an apparent pupil width of 1.5 mm and to a size of pupil in the iris of 1.34 mm).

The values stated in the description for transmittance are in each case the values of the directed transmittance at perpendicular radiation ingress (which generally is less than scattered transmittance).

List of Symbols:

$\tau(\lambda)$: Spectral transmittance of the radiation protection filter $\tau_1$: Mean transmittance of the radiation protection filter from 250–300 nm $\tau_2$: Mean transmittance of the radiation protection filter from 300–340 nm $\tau_3$: Mean transmittance of the radiation protection filter from 340–400 nm $\tau_4$: Mean transmittance of the radiation protection filter from 340–400 nm $\tau_i(\lambda)$: Internal transmittance at wavelength $\lambda$ $\tau_{i,1}(\lambda)$: Known internal transmittance of the radiation protection filter at wavelength $\lambda$ and additive concentration $k_1$ $\tau_{i,2}(\lambda)$: Desired transmittance of the radiation protection filter at wavelength $\lambda$ and additive concentration $k_2$ $\tau_{vis}$: Light transmittance of the radiation protection filter between 380 and 780 nm $R_F$: Correction factor of the radiation protection filter $\phi_{30}$: Radiant flux in the 340–400 nm range that penetrates the eye lens in the case of unprotected eyes [$\mu$W]

$\phi_{31}$: Radiant flux in the 340–400 nm range that penetrates the eye lens in the case of eyes protected with the radiation protection filter [$\mu$W]

$E(\lambda)$: Spectral power distribution of the global radiation (approximately corresponding to the calorimetric standard illuminants D 65 or C)

$E_{p,30}$: Irradiance in the pupillary plane in the 340–400 nm range with unprotected eyes [W m$^{-2}$]

$E_{p,31}$: Irradiance in the pupillary plane in the 340–400 nm range with eyes protected with the radiation protection filter [W m$^{-2}$]

$f_3$: Cornea-pupil coefficient for irradiance in the 340–400 nm range $E_{30}$: Cornea irradiance in the 340–400 nm range with unprotected eyes [W m$^{-2}$]

$E_{31}$: Cornea irradiance in the 340–400 nm with eyes protected with the radiation protection filter [W m$^{-2}$]

$E_{vis}$: Cornea illumination [1×]

$E_{vis,o}$: Cornea illumination with unprotected eyes [1×]

$E_{vis,1}$: Cornea illumination with eyes protected with the radiation protection filter [1×]

F: Pupillary surface area (size of the pupil in the iris) [mm$^2$]

$F_o$: Pupillary surface area (size of the pupil in the iris) with unprotected eyes [mm$^2$]

$F_1$: Pupillary surface area (size of the pupil in the iris) with eyes protected with the radiation protection filter [mm$^2$]

$v(\lambda)$: Relative luminous efficiency for photopic vision.

I claim:

1. Radiation protection filter for skin pigmentation during solar irradiation characterized by the following features:
   (a) in the wavelength range between 300 and 340 nm, the mean transmittance ($\tau_2$) of the radiation protection filter is at the very most 0.1;
   (b) in the wavelength range between 340 and 400 nm, the mean transmittance ($\tau_3$) of the radiation protection filter is between 0.35 and 0.55;
   (c) in the wavelength range between 340 and 440 nm, the mean transmittance ($\tau_4$) of the radiation protection filter is between 0.45 and 0.7;
   (d) in the wavelength range between 380 and 780 nm, the light transmittance ($\tau_{vis}$) of the radiation protection filter is such that, when the radiation filter is used, the amount of radiation in the range between 340 and 400 nm that penetrates the eye lens is, at the very most, that amount of radiation in the 340–400 nm range that penetrates the eye lens when the radiation protection filter is not used.

2. Radiation protection filter according to claim 1, characterized in that the light transmittance ($\tau_{vis}$) of the radiation protection filter is at the least equivalent to the following value:

$$\tau_{vis} = \tau_3^2 - \frac{(1 - \tau_3)^2}{10}$$

3. Radiation protection filter according to claim 1, characterized in that the mean transmittance ($\tau_1$) of the radiation protection filter in the wavelength range between 250 and 300 nm is at the very most equal to the mean transmittance ($\tau_2$) in the wavelength range between 300 and 340 nm.

4. Radiation protection filter according to claim 1 wherein said mean transmittance of said filter in the wavelength range between 300 and 340 nm is at the very most 0.01.

5. Radiation protection filter according to claim 1 wherein said transmittance of said filter in the wavelength range between 300 and 340 nm is at the very most 0.001.

6. Radiation protection filter according to claim 1 characterized in that the light transmittance of said filter is at the very most 0.4.

7. Radiation protection filter according to claim 1 characterized in that the light transmittance of said filter is at the very most 0.35.

* * * * *

UNITED STATES PATENT AND TRADEMARK OFFICE
CERTIFICATE OF CORRECTION

PATENT NO. : 4,783,142
DATED : November 8, 1988
INVENTOR(S) : Maximilian F. Mutzhas It is certified that error appears in the above-identified patent and that said Letters Patent is hereby corrected as shown below:

Column 3, line 27, change "transmittance" to -- transmittances --.

Column 3, line 35, change "pound" to -- pounds --.

Column 7, line 9, change "whiich" to -- which --.

Column 8, line 49, insert -- mean -- after "said" (first occurrence).

Signed and Sealed this

Second Day of May, 1989

*Attest:*

DONALD J. QUIGG

*Attesting Officer*     *Commissioner of Patents and Trademarks*